(12) United States Patent
Chabloz et al.

(10) Patent No.: US 9,987,152 B2
(45) Date of Patent: *Jun. 5, 2018

(54) PROSTHESIS FOR A LOWER LIMB

(71) Applicant: OTTO BOCK HEALTHCARE GMBH, Duderstadt (DE)

(72) Inventors: Pierre Chabloz, Saint Georges de Commiers (FR); Christian Will, Gottingen (DE); Martin Pusch, Duderstadt (DE); Herman Boiten, Gottingen (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/525,007

(22) Filed: Oct. 27, 2014

(65) Prior Publication Data

US 2015/0112449 A1    Apr. 23, 2015

Related U.S. Application Data

(63) Continuation-in-part of application No. 13/315,827, filed on Dec. 9, 2011, now Pat. No. 8,870,969.

(30) Foreign Application Priority Data

Dec. 9, 2010 (FR) .................................... 10 04800

(51) Int. Cl.
*A61F 2/64* (2006.01)
*A61F 2/62* (2006.01)
(Continued)

(52) U.S. Cl.
CPC .................. *A61F 2/80* (2013.01); *A61F 2/64* (2013.01); *A61F 2002/502* (2013.01); *A61F 2002/5006* (2013.01); *A61F 2002/5009* (2013.01); *A61F 2002/5021* (2013.01); *A61F 2002/5033* (2013.01); *A61F 2002/5038* (2013.01);
(Continued)

(58) Field of Classification Search
CPC ................ A61F 2/64–2/646; A61F 2002/6854
See application file for complete search history.

(56) References Cited

U.S. PATENT DOCUMENTS 5,387,246 A   2/1995  Phillips
5,645,590 A   7/1997  van de Veen
(Continued)

FOREIGN PATENT DOCUMENTS

DE    452 187    * 11/1927    .............. A61F 2/64
DE    502 697    *  7/1930    .............. A61F 2/64
(Continued)

*Primary Examiner* — David H Willse
(74) *Attorney, Agent, or Firm* — Holland & Hart LLP

(57) ABSTRACT

A prosthesis for a residual limb includes an element for receiving a stump fitted on or established by a support part, a distal prosthetic part, and an absorbing system. The distal prosthetic part is assembled on the support part by a pivot link forming a joint to enable flexion or extension of the distal prosthetic part with respect to the element for receiving. The absorbing system absorbs the flexion or extension efforts and is connected to the distal prosthetic part and to one of a rod or a lever that is pivotally fitted on the distal prosthetic device. The rod is mounted to the lever and to the support part.

23 Claims, 20 Drawing Sheets

(51) Int. Cl.
- *A61F 2/68* (2006.01)
- *A61F 2/80* (2006.01)
- *A61F 2/56* (2006.01)
- *A61F 2/50* (2006.01)
- *A61F 2/60* (2006.01)
- *A61F 2/70* (2006.01)
- *A61F 2/74* (2006.01)

(52) U.S. Cl.
CPC . *A61F 2002/5075* (2013.01); *A61F 2002/607* (2013.01); *A61F 2002/6854* (2013.01); *A61F 2002/701* (2013.01); *A61F 2002/74* (2013.01)

(56) References Cited

U.S. PATENT DOCUMENTS

| | | |
|---|---|---|
| 7,278,522 B2 | 10/2007 | Reinhardt et al. |
| 2007/0050044 A1 | 3/2007 | Haynes et al. |
| 2007/0162152 A1 | 7/2007 | Herr et al. |

FOREIGN PATENT DOCUMENTS

| | | | | |
|---|---|---|---|---|
| EP | 1417942 A2 | 5/2004 | | |
| EP | 1598573 A1 | 11/2005 | | |
| GB | 158096 | * | 1/1921 | ............. A61F 2/604 |
| GB | 1007431 | * | 10/1965 | ............... A61F 2/64 |
| SU | 1801416 A1 | 3/1993 | | |

* cited by examiner

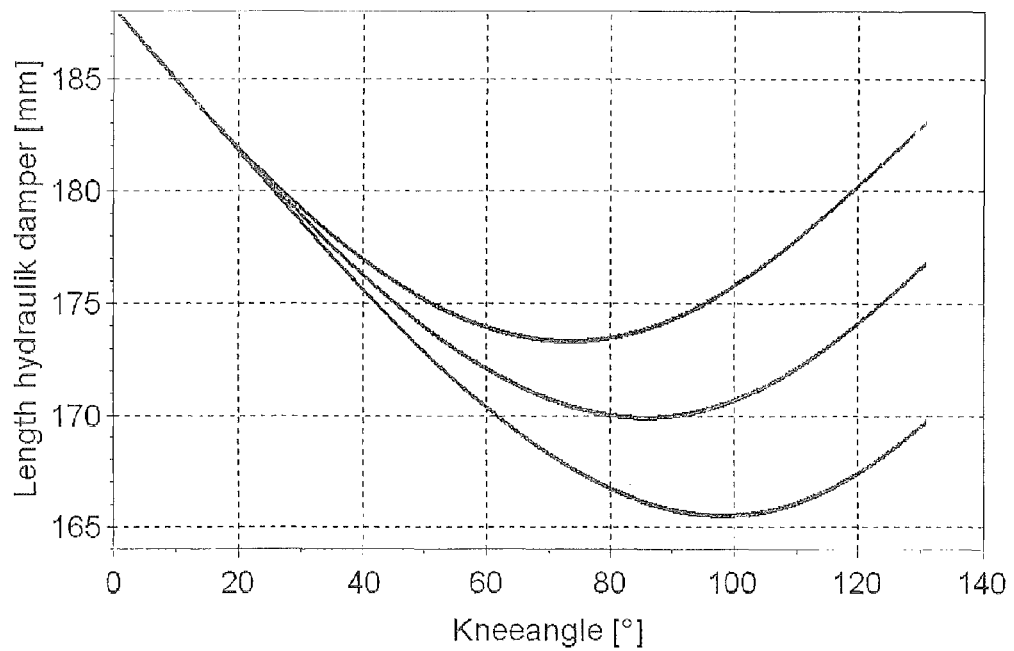
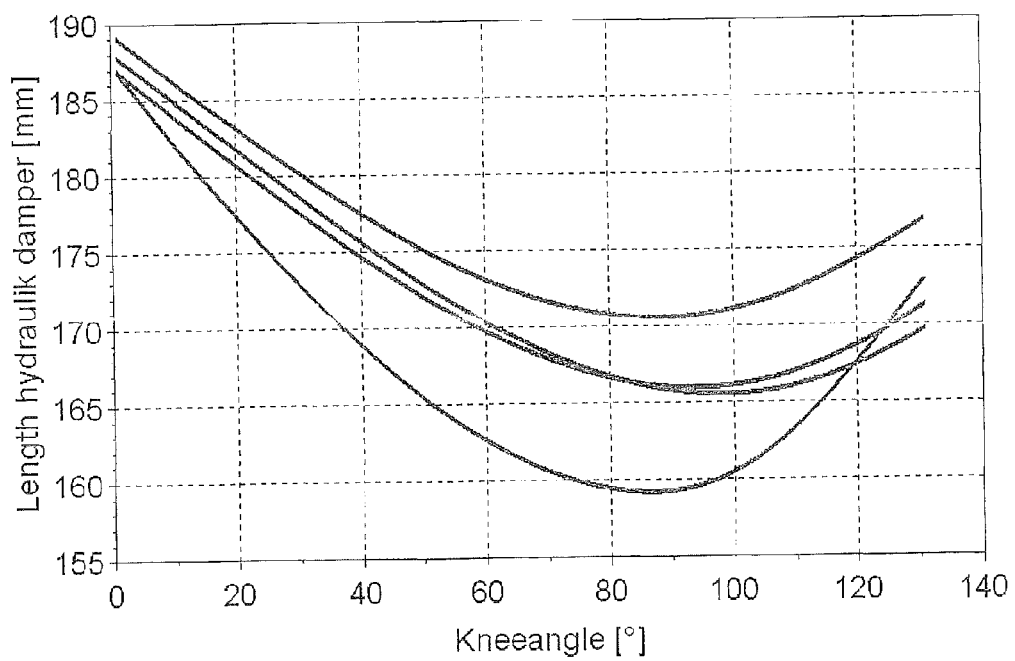
Fig. 16

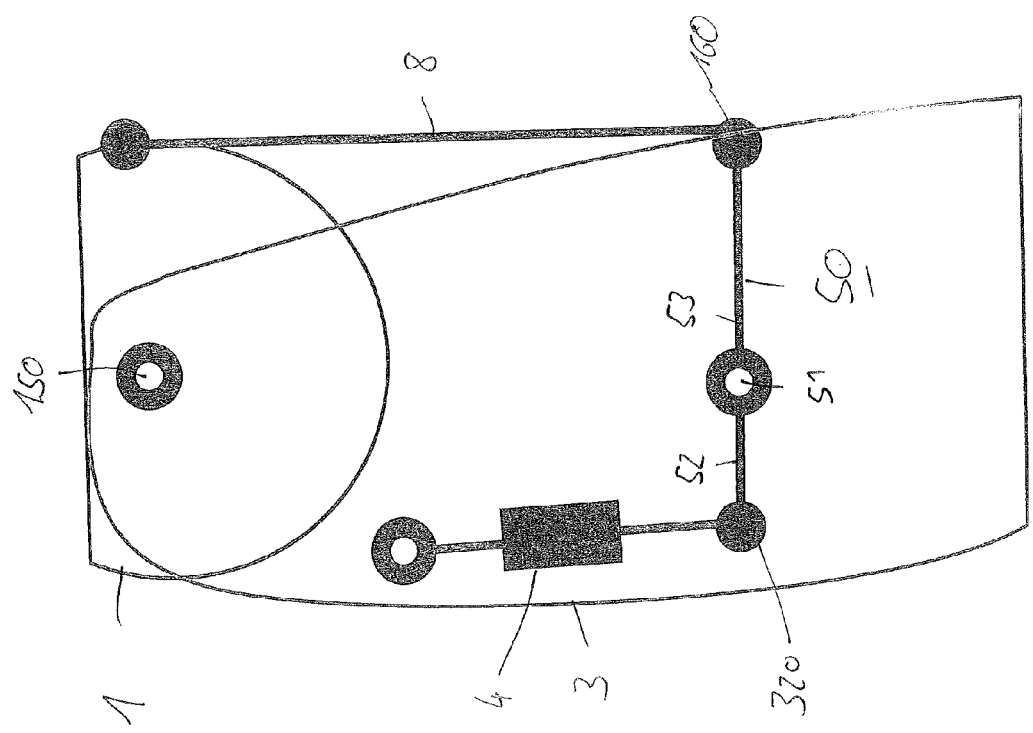

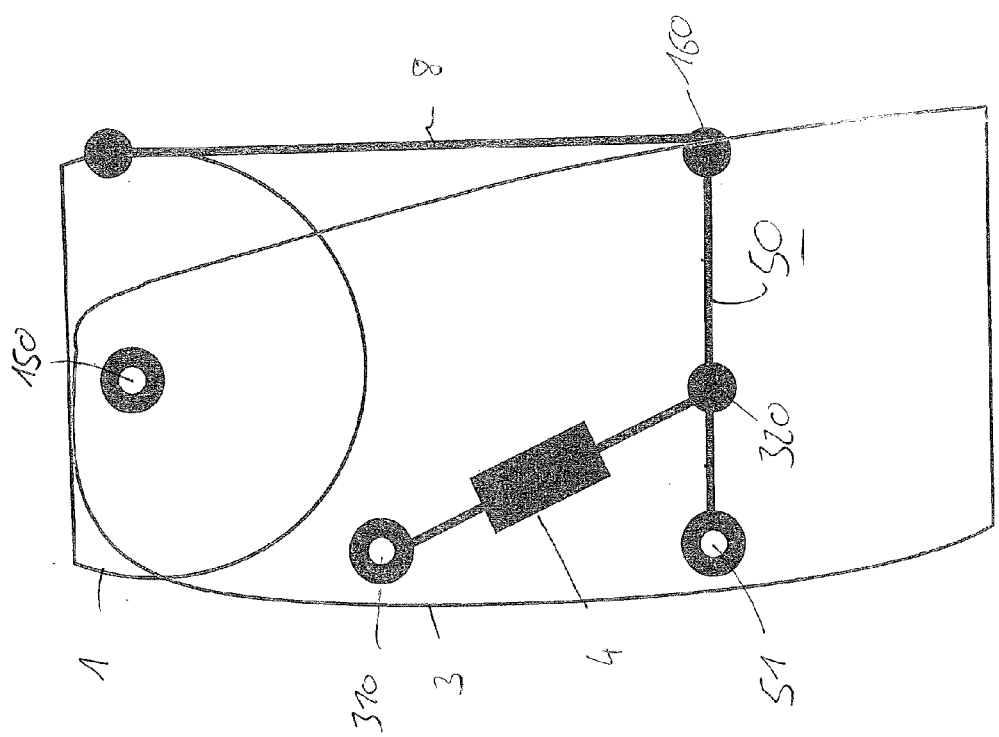

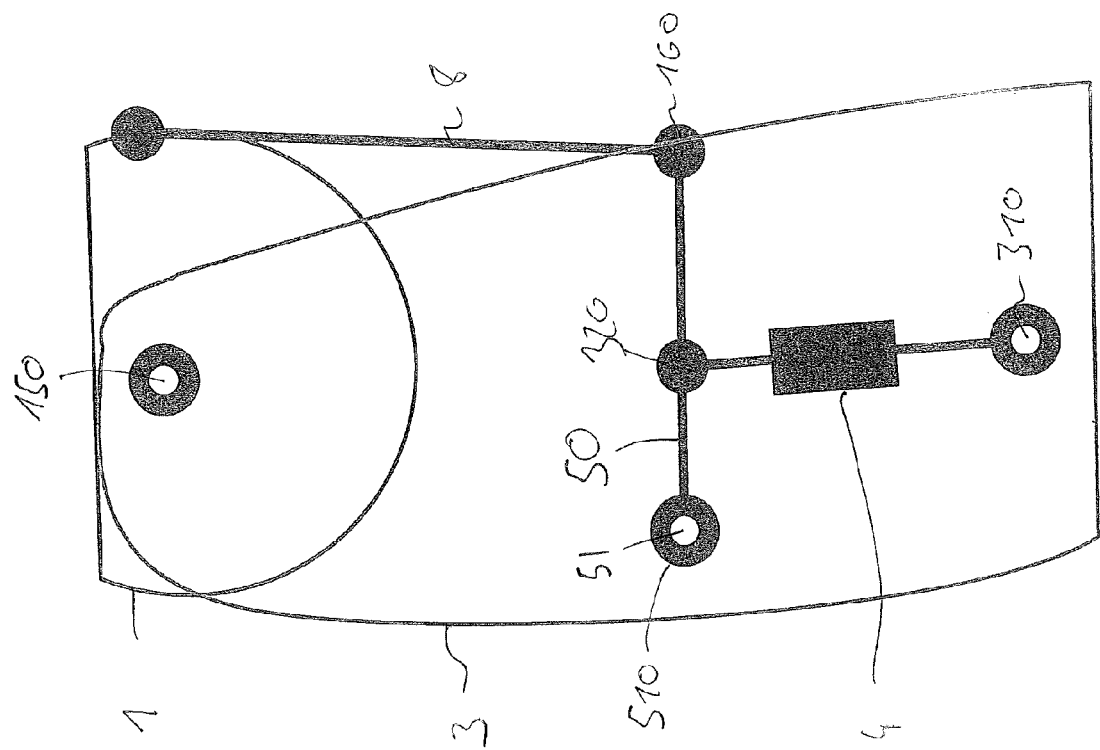

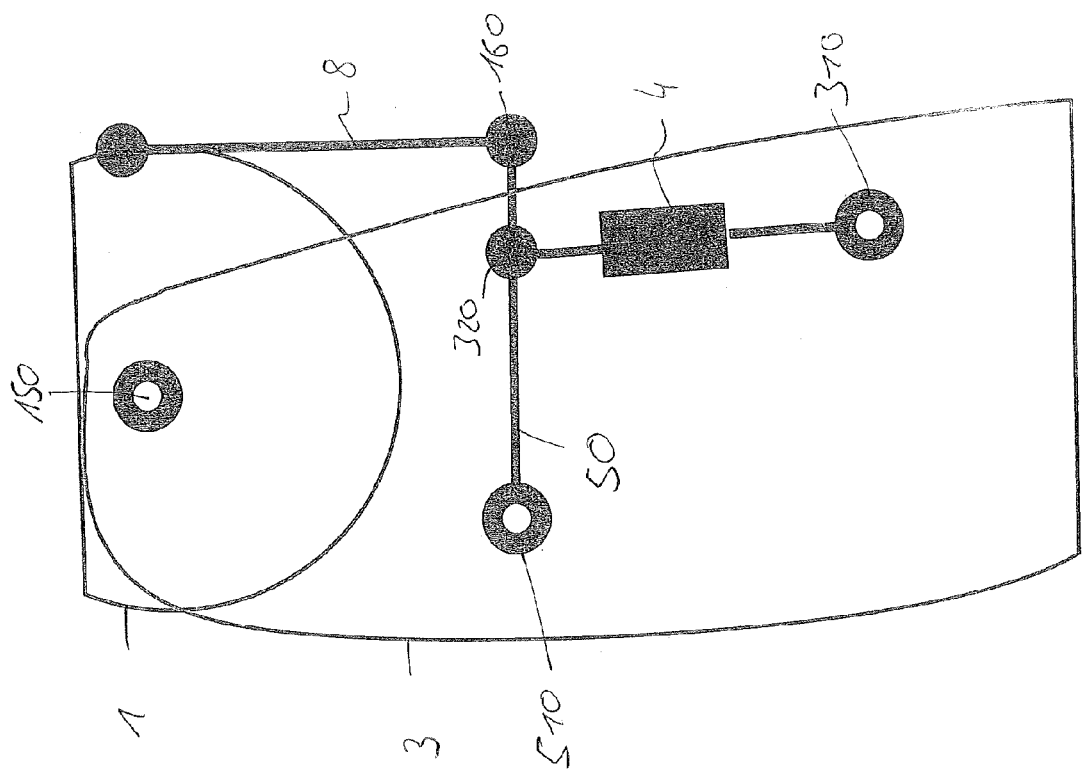

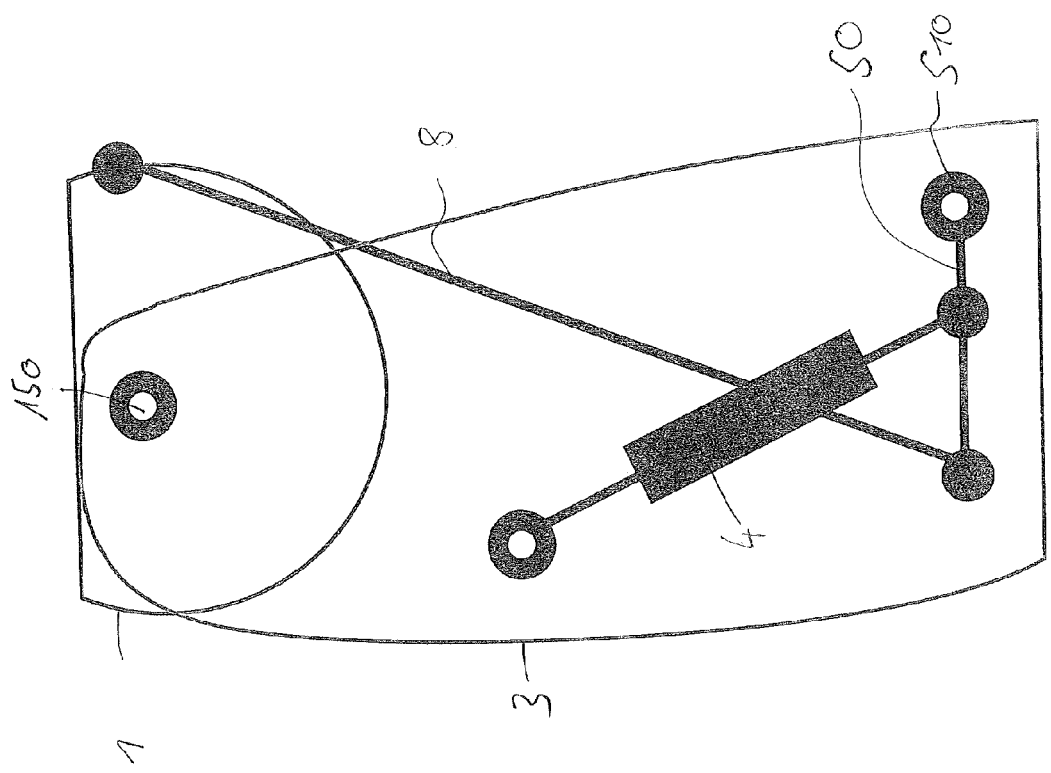

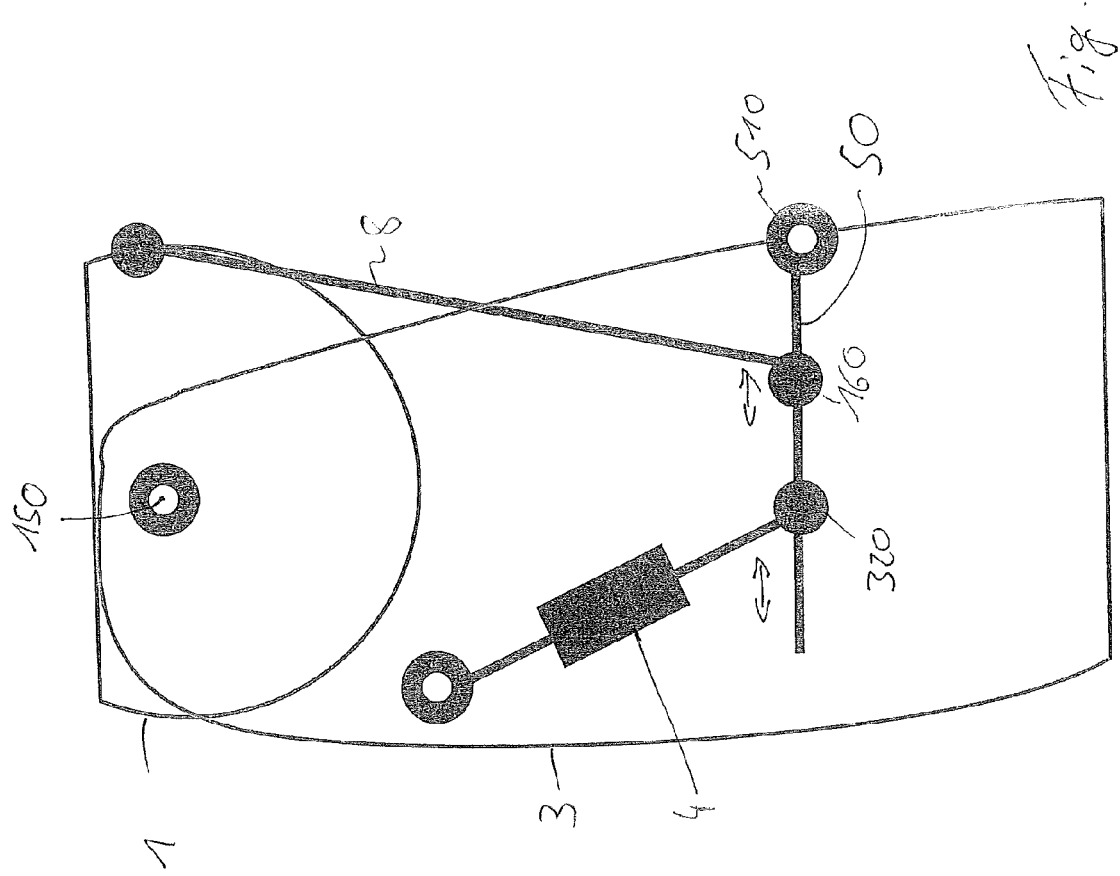

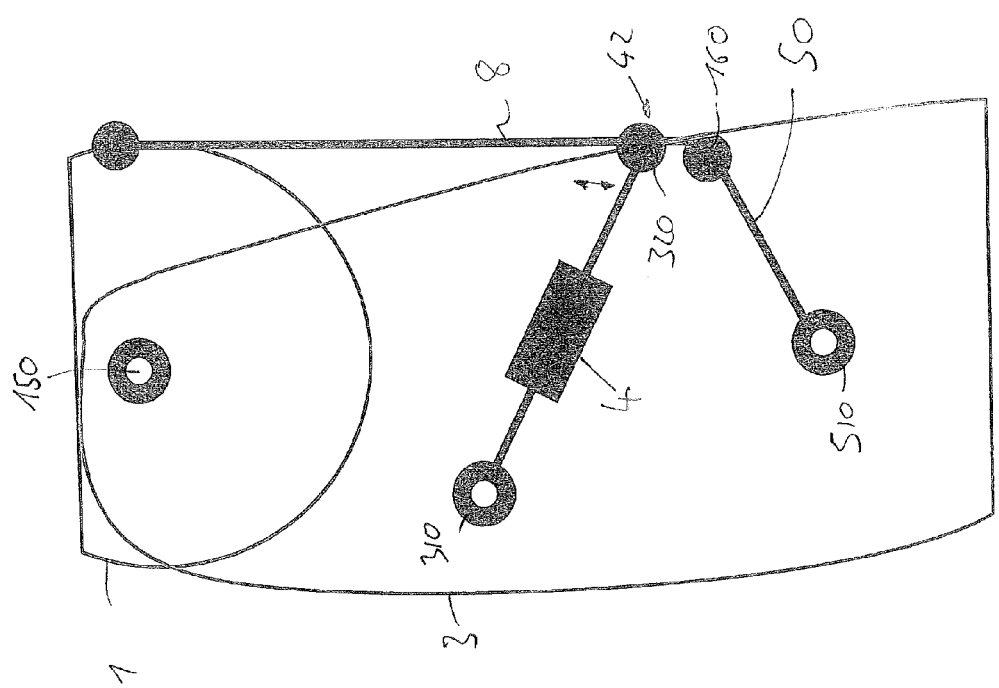

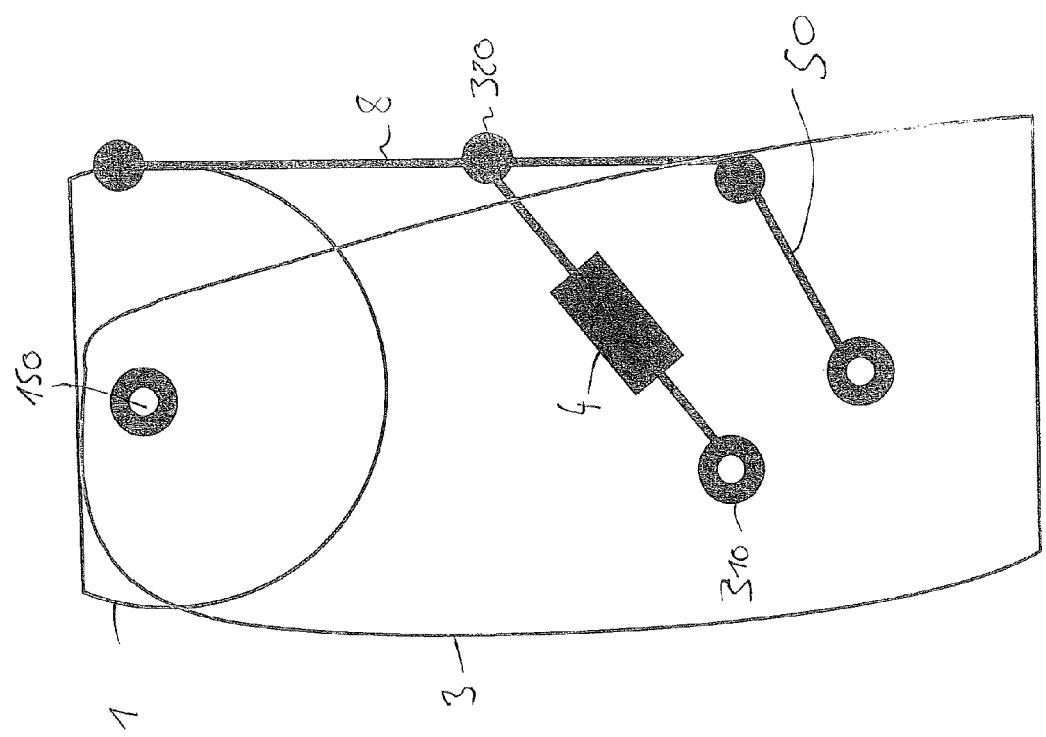

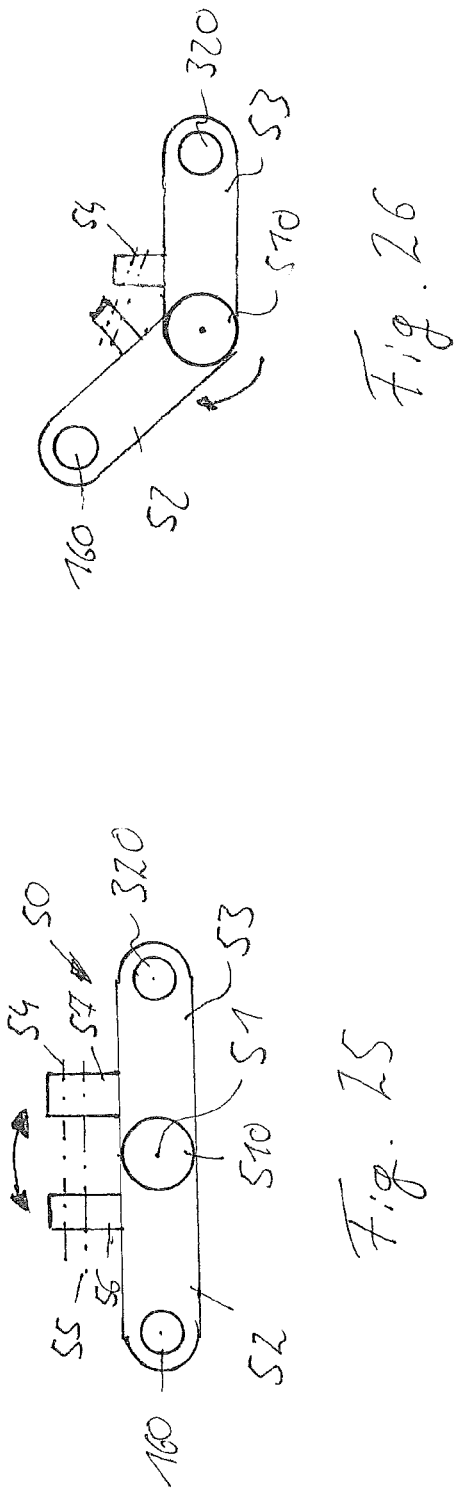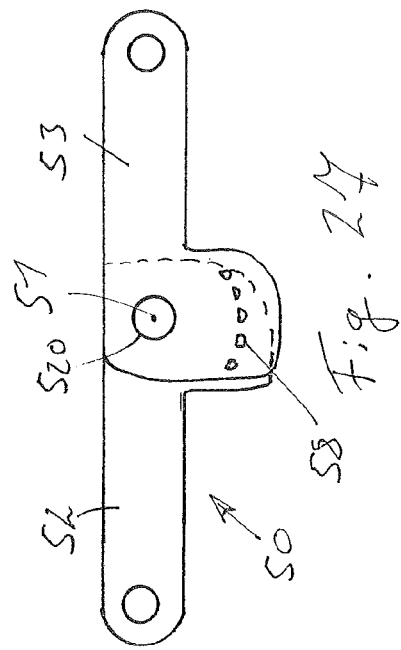

PROSTHESIS FOR A LOWER LIMB

CROSS REFERENCE TO RELATED APPLICATIONS

This application is a continuation-in-part of U.S. application Ser. No. 13/315,827, filed 9 Dec. 2011, and issued 28 Oct. 2014 as U.S. Pat. No. 8,870,969, which claims the benefit of French Patent Application 1004800, filed 9 Dec. 2010, the disclosures of which are incorporation herein, in their entireties, by this reference.

BACKGROUND

The present disclosure generally relates to a prosthesis comprising an element for receiving a stump fitted on or established by a support part, a distal prosthetic part assembled on said support part by a pivot link forming a pivot joint to enable flexion or extension of the distal prosthetic part with respect to the support part, and an absorbing system to absorb the flexion or extension efforts.

Persons having a lower limb amputated between the knee and the hip have already been offered the possibility of being able to ski again.

In a first approach, amputated persons skied on a single leg and were equipped with crutches provided with small skis at their ends for them to be able to keep their balance.

In a second approach, it was proposed to give amputated persons the possibility of skiing on two lower limbs with a prosthetic material performing functions close to those of a real lower limb under particular conditions, such as the triple flexion position (hip, knee, ankle) with an absorber enabling the contours of a ski slope to be absorbed.

Articulated prostheses for the lower limb comprising an element for receiving a thigh stump of a patient thus exist. The element can then be fitted onto a leg by a pivot link the pin of which forms a knee joint to enable flexion or extension of the leg with respect to the element. A jack enables the flexion or extension efforts to be absorbed.

In the example of FIGS. 1 and 2, a support part 1, on which the element for receiving 6 are fitted, is itself fitted on leg 3 by a pivot link 2 so as to form a knee joint. Jack 4 is fitted on the one hand on a front part of leg 3 (part facing a foot 5), and on the other hand on a rear part (zone at the level of which the angle a, closes in case of flexion) of support part 1.

FIG. 1 illustrates the position of the prosthesis in flexion with an angle a of 155 degrees between leg 3 and element for receiving 6 at the level of the flexion. FIG. 2 illustrates an angle a of 110 degrees. With angle [alpha] at 155 degrees, the force Fjack exerted by jack 4 is about 2500 Newton whereas at 110 degrees the force Fjack exerted by the same jack 4 is about 5100 N. The more the prosthesis is flexed, the more the jack will in fact have difficulty in counteracting the flexion, and the user then finds him/herself without a shock absorbing system which may lead to breaking at the level of the joint. Furthermore, the convenience of use of the prosthesis is thereby greatly impaired.

SUMMARY

The object of the invention is to provide a more solid prosthesis that has a behavior close to that of a valid limb, especially for relative long stumps or patients with a disarticulation.

This object tends to be achieved by the appended claims and in particular by the fact that the absorbing system is fitted on the one hand on the distal prosthetic part and on the other hand on a lever pivotally fitted on the distal prosthetic device or on a rod, said rod mounted on the one hand on the lever and on the other hand on the support part.

Such a fitting also results in a compact design and the possibility to locate the absorbing system at various points, leading to an optimized design and a leverage of the forces acting on the absorbing system.

In one aspect of the invention, the absorbing system comprises at least one of the following devices: a dampening device, a spring device, and an actuator device. The dampening device may be designed as a hydraulic damper or as a pneumatic damper or as a combination of hydraulic and pneumatic damper. The spring device may be designed as a single spring or a combination of two or more springs. The springs can be designed as coil springs, helical springs, leaf springs or disk springs as well as elastomer parts. The actuator device may be designed as an electric motor, a magnetic motor or magnetic actuator, a linear actuator, or a hydraulic motor.

In one aspect of the invention, the support part is a prosthetic shaft, a cup shaped receiving element configured to be connected with a prosthetic shaft or a liner, or an osseointegratable device.

In one aspect of the invention, the lever comprises two lever arms on opposing sides of a pivot axis to establish a rocker, the absorbing system being fitted on a first lever arm, and the rod being fitted on a second lever arm.

In one aspect of the invention, the lever comprises a single lever arm, and the absorbing system is fitted on the lever arm spaced apart from a fitting point of the rod on the lever arm.

In one aspect of the invention, the absorbing system or the rod are displaceably fitted on the lever.

In one aspect of the invention, the rod, the lever, or the absorbing system is variable in its length.

In one aspect of the invention, the distal prosthetic device is hollow with an inner space in which the lever and the absorbing system are at least partially arranged.

In one aspect of the invention, the rod covers an opening in the distal prosthetic part at least partially.

In one aspect of the invention, the rod is formed to complete an appearance of a natural limb.

In one aspect of the invention, the joint comprises a joint axis, and the joint axis runs through the support part.

In one aspect of the invention, the joint comprises a joint axis, and the joint axis is arranged in an area of a joint axis of a natural limb.

In one aspect of the invention, the joint comprises a joint axis, and the joint axis is arranged proximal to a distal end of the support part.

In one aspect of the invention, the distal prosthetic part is directly mounted on the support part at at least one bearing point, whereas the at least one bearing point is medially or laterally positioned on the support part.

In one aspect of the invention, the at least one bearing point is displaceably mounted on the support part.

In one aspect of the invention, the rod is displaceably mounted on the support part.

In one aspect of the invention, a locking device is provided to lock the flexion or extension of the joint.

In one aspect of the invention, the lever comprises two lever parts, and the lever parts are displaceably fitted to each other.

In one aspect of the invention, the lever parts are pivotally fitted to each other, and the pivot axis of the lever parts aligns with the pivot axis of the lever.

In one aspect of the invention, the prosthesis is a prosthesis for a lower limb, the support part is for receiving a thigh stump or a thigh shaft, the pivot link forming a knee joint, and the distal prosthetic part is a shank part. Alternatively, the prosthesis is a prosthesis for an upper limb, wherein the distal prosthetic part replaces the lower arm and the pivot link forms an cubital joint. Furthermore, the prosthesis may be designed as a foot prosthesis.

BRIEF DESCRIPTION OF THE DRAWINGS

Other advantages and features will become more clearly apparent from the following description of particular embodiments of the invention, given for non-restrictive example purposes and represented in the appended drawings in which:

FIG. 16 illustrates dampening characteristics over a knee angle depending on the length of a damper.

FIGS. 17 to 24 illustrate schematic views of different embodiments of the invention.

FIGS. 25 to 27 illustrate schematic view of multi-part rockers.

DETAILED DESCRIPTION

The prosthesis described in the following differs from the prosthesis according to the prior art in that its particular assembly enables the efforts of the absorbing system to be limited.

What is meant by lower limb of a person is a thigh, a knee and a foot. The thigh is the part situated between the hip and the knee, and the leg is the part situated between the knee and the instep.

Figure 1:
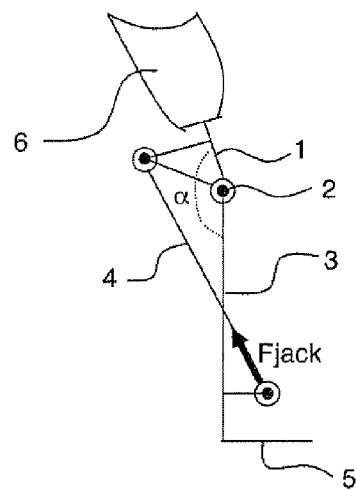
FIGS. 1 and 2 schematically illustrate devices of the prior art in distinct positions.
Figure 2:
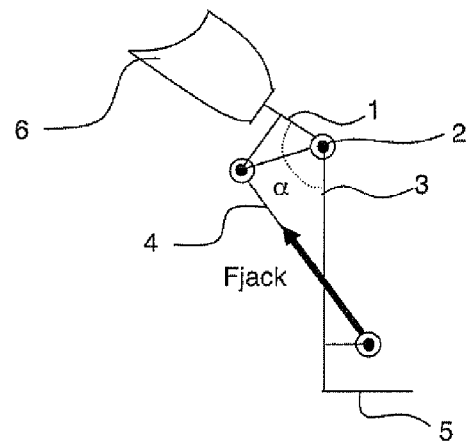
Figure 3:
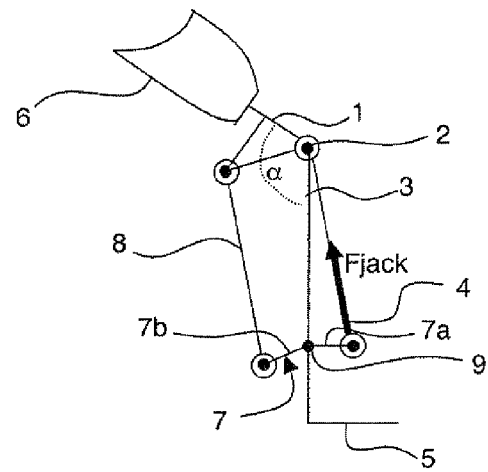
FIG. 3 schematically illustrates a particular device according to the invention.

FIG. 3 schematically illustrates a prosthesis for a lower limb comprising element for receiving 6 a thigh stump fitted on a support part 1. A leg 3 is assembled on said support part 1 by means of a pivot link 2 forming a knee joint to enable flexion or extension of leg 3 with respect to the element for receiving 6 (at angle [alpha], in FIG. 3). A absorbing system 4, enabling the flexion or extension efforts to be absorbed, is fitted on the one hand on the pin of pivot link 2 and on the other hand on a first end of a rocker 7 pivotally mounted on leg 3. A rod 8 is fitted on the one hand on a second end of rocker 7 and on the other hand on support part 1 so as to transmit the pivoting movement of the support part around the pin of pivot link 2 to the rocker to solicit the absorbing system more or less.

When support part 1 pivots around the pin of pivot link 2, rod 8 transmits the pivoting to the rocker, thereby transmitting the movement to the absorbing system 4 decreasing, or increasing, the distance separating the assembly point of absorbing system on rocker 7 from the assembly point at the level of the pin (also called "axis" in the domain) of pivot link 2. In other words, the smaller the angle a is, the more the absorbing system will be compressed, i.e. in case of flexion, the distance separating the assembly point of said system 4 on the rocker will move towards the pin of pivot link 2. Naturally, the respective assembly points of absorbing system 4 and of rod 8 at the level of the rocker are advantageously situated at the ends of rocker 7 arranged on each side of swivel pin 9 of rocker 7. Furthermore, in the particular implementation, the assembly point of rod 8 at the level of support part 1 is situated on the same side as the assembly point of rod 8 on rocker 7.

In other words, rocker 7 can comprise two branches 7a, 7b on each side of its swivel pin 9. A first branch 7a is directed towards a first surface called front surface of the prosthesis (the front surface is in fact the surface of the prosthesis facing a foot 5). A second branch 7b is directed towards a second surface, opposite the first surface, and called rear surface of the prosthesis (the rear surface of the prosthesis corresponds to the rear face of a lower limb, i.e. the face which will enable element for receiving 6 to be moved towards leg 3 by flexion). In the particular example of FIG. 3, absorbing system 4 is fitted on first branch 7a of rocker 7 at an end of first branch 7a proximal to the front surface of the prosthesis. Rod 8 is fitted on second branch 7b of rocker 7, at an end of rocker 7 proximal to the rear surface of the prosthesis, and fitting of rod 8 at the level of support part 1 is performed at the level of the rear surface of the prosthesis.

Figure 4:
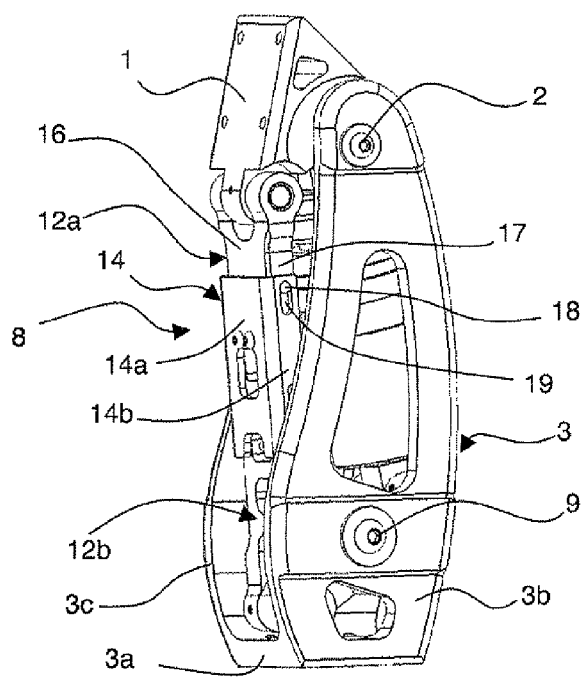
FIG. 4 illustrates a view in three dimensions of the leg and of the support part in the flexion position.
Figure 5:
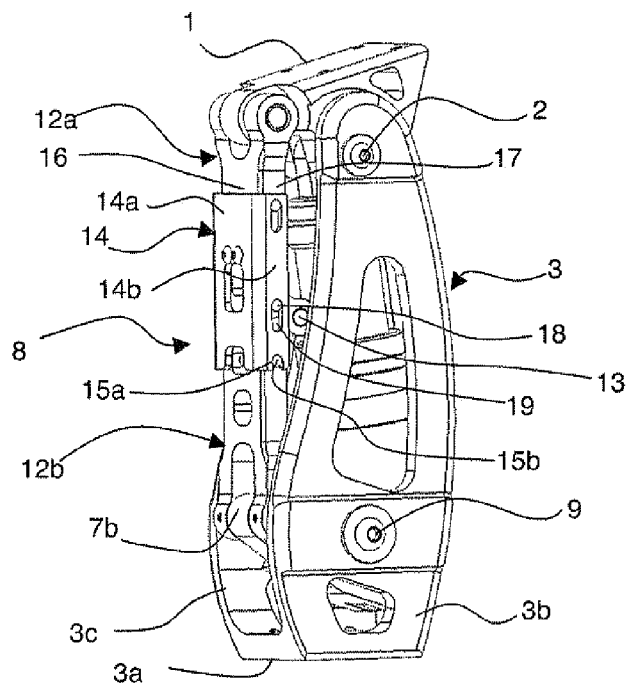
FIG. 5 illustrates a view in three dimensions of the leg and of the support part in the extension position.

FIGS. 4 and 5 illustrate a particular embodiment. According to this particular embodiment, leg 3 can have a monoblock main part comprising a base 3a connecting two uprights 3b, 3c substantially parallel to one another.

At the end of leg 3 distal from base 3a, a pin can be fitted so as to connect the two uprights 3a, 3b, preferably perpendicularly. This pin can be fixed with respect to uprights 3b, 3c. Support part 1 is pivotally mounted on this pin, designed to form pivot link 2 referred to in the foregoing.

Figure 6:
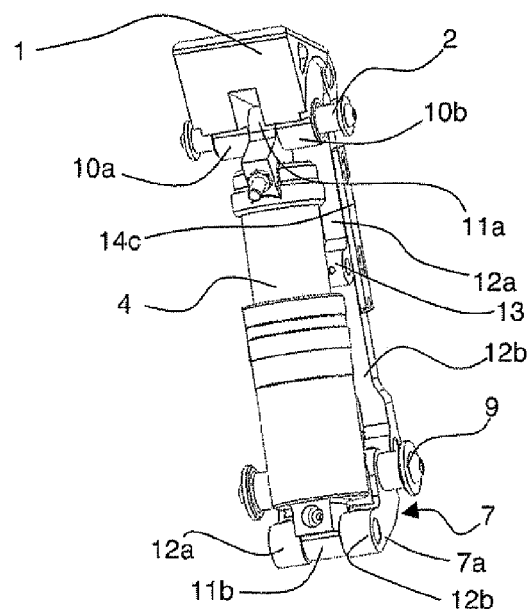
FIG. 6 illustrates a view in three dimensions of the leg and of the support part without the main body of the leg.

Support part 1 can be a part which is for example monoblock, comprising a first assembly zone designed to receive the pin of pivot link 2 and a second assembly zone designed to receive a pin for fixing one end of rod 8. As illustrated in FIG. 6 in which the main body of leg 3 has been removed for the sake of clarity, the first assembly zone can comprise two sections 10a, 10b each comprising a bore, the bores of said sections 10a, 10b being coaxial. The two sections 10a, 10b are separated by an empty space, between the two sections 10a, 10b, designed to receive one end of absorbing system 4 equipped with a first assembly part 11a comprising a bore designed to receive the pin of pivot link 2. Thus, in the assembled position, the pin of pivot link 2 passes through the two bores of sections 10a, 10b of support part 1, and the bore of first assembly part 11a.

In FIGS. 4 and 5, the pin of pivot link 2 of the joint is fixed at the level of the two uprights 3b, 3c of leg 3, and support part 1 and absorbing system 4 are mounted with swiveling/rotation on the pin of pivot link 2 between the two uprights 3b, 3c.

Figure 7:
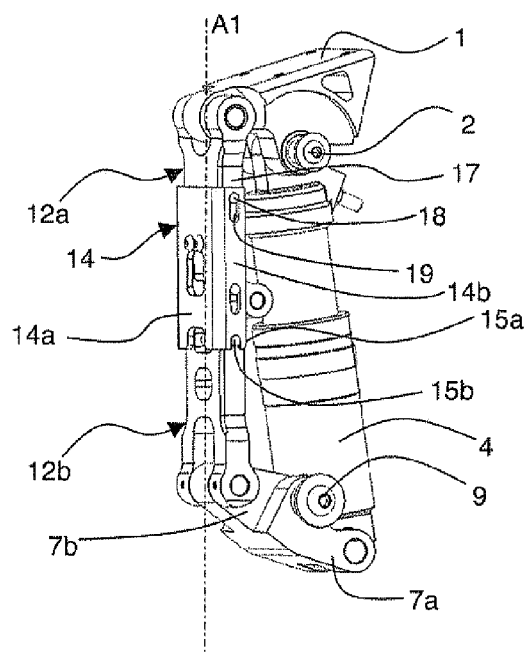
FIG. 7 illustrates a different view of FIG. 6.

Rocker 7 can be secured to said to uprights 3b, 3c by swivel pin 9 between the two uprights 3b, 3c, and preferably in proximal manner to base 3a, (FIGS. 4 to 6). Rocker 7 then comprises two distal ends formed by branches 7a, 7b visible in FIG. 7, a first end being directed towards the front part of leg 3 and a second end being directed towards the rear part of leg 3. The first end is designed for fitting of absorbing system 4. Absorbing system 4 can be fitted on this first end by means of an associated pivot link. In the particular example of FIG. 6, at its first end, the rocker comprises two sections of rocker 12a, 12b separated by an empty space, forming a Y. Between the two sections of rocker 12a, 12b, a second assembly part 11b (FIG. 6) of absorbing system 4 is inserted in such a way that a common pin can be inserted in the bores respectively formed at the level of the two sections 12a, 12b of rocker and of second assembly part 11b.

The second end of rocker 7 is designed for fitting of rod 8. Rod 8 can be fitted on this second end by means of a pin forming a pivot link. In other words, at its second end, the rocker can comprise a bore receiving a pin on which rod 8 can be fitted.

Opposite its fitting point on rocker 7, rod 8 can be mounted pivoting around a pin arranged at the rear (rear surface of the prosthesis) of support part 1, said pin being able to be fixed with respect to support part 1. In FIGS. 4 and 5, rod 8 can comprise two distal ends in the form of a Y so as to respectively receive a part of rocker 7 and a part of support part 1 in the space separating the two branches of the Y, thereby enabling assembly to be performed by means of corresponding pins. The parts of the rocker and of support part 1 each comprise a bore designed to receive a pin forming an assembly point of rod 8.

In the particular example of FIGS. 4 and 5, for rod 8, the pin at the level of the rocker is fixed with respect to rod 8, enabling swiveling of the rocker around this pin. The pin at the level of support part 1 is fixed with respect to support part 1, enabling swiveling of rod 8 around this pin. For the absorbing system, it is fitted swiveling on the pin of pivot link 2 and on the pin acting as assembly point on the rocker, said assembly pin being fixed with respect to it the rocker.

Figure 8:
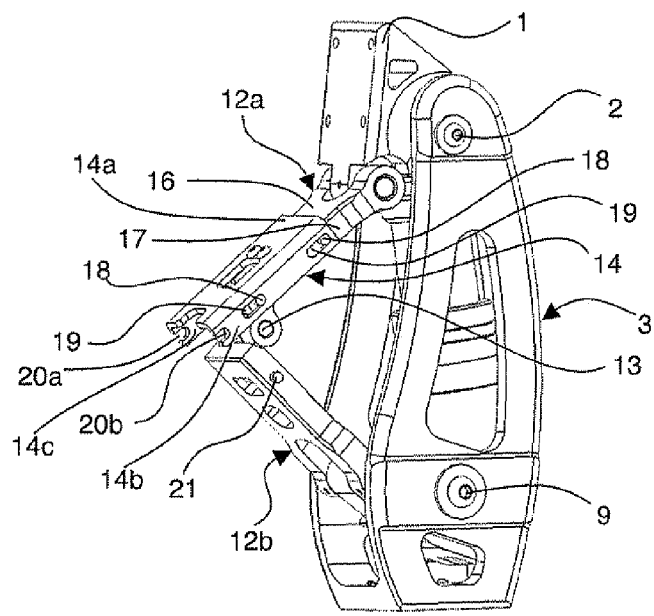
FIG. 8 illustrates a view in three dimensions in which the rod is disengaged.
Figure 9:
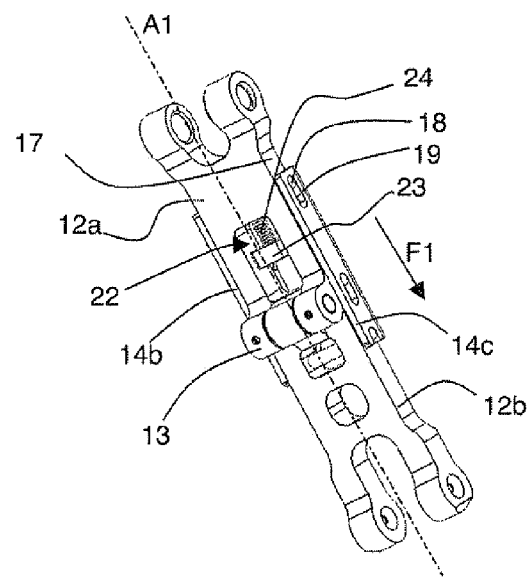
FIG. 9 illustrates the rod used according to a particular embodiment.

According to a particular embodiment, rod 8 can be arranged so as to occupy a first position in which the swiveling movement of support part 1 with respect to leg 3 is transmitted to rocker 7, and a second position (FIG. 8) in which said movement is not transmitted to rocker 7 (FIGS. 4 and 5). This can for example be achieved by a rod 8, as illustrated in FIG. 9, comprising a first plate 12a (or element) mounted on support part 1 (FIGS. 4 to 8) and a second plate 12b (or element) mounted on rocker 7. First plate 12a forms a hinge 13 with second plate 12b. In other words, first plate 12a is pivotally mounted on second plate 12b to prevent transmission of a movement of support part I to rocker 7, should such a movement take place. Hinge 13 can be formed on the median of rod 8, perpendicularly to the longitudinal axis A1 of said rod 8.

This rod 8 with two positions presents an advantage when the prosthesis is used for skiing. In a first position, the skier can in fact solicit the prosthesis when descending a slope, and when he/she embarks on a ski lift, the prosthesis can move to the second position of rod 8 enabling the skier to sit down without difficulty on the seat of the ski lift as the absorbing system 4 is deactivated.

Rod 8 preferably comprises latching means arranged so as to prevent swiveling of first plate 12a with respect to second plate 12b in the first position and to enable said swiveling in the second position.

FIGS. 5 to 9 illustrate a particular embodiment of such latching means. The latter can comprise a mounting plate 14 fitting sliding on one of plates 12a, 12b, preferably on the rear surface of the prosthesis, in a plane parallel to the plane of the associated plate. At one end, mounting plate 14 preferably comprises first engagement means 15a collaborating in the first position with second engagement means 15b of the other plate to latch the first and second plates to one another. In the first position, the first and second plates are deprived of relative movements with respect to one another. In other words, the two plates behave as a monoblock part. In the second position, first plate 12a can swivel with respect to second plate 12b, for example at the level of hinge 13, so as not to transmit the movement from support part 1 to rocker 7, this enabling the stresses imposed on absorbing system 4 to be relaxed.

In a particular example of FIGS. 4 to 9, mounting plate 14 comprises a base 14a joining two parallel opposite sides walls 14b, 14c, oriented in the longitudinal direction (axis A1 in FIGS. 7 and 9) of rod 8 in the first position. A transverse dimension of base 14a is larger than the transverse dimension of first plate 12a so that base 14a snugly follows a main surface 16 of said first plate 12a. In the example, main surface 16 is substantially parallel to the plane of first plate 12a. The two opposite sides walls 14b, 14c each respectively snugly follow an edge 17 of the first plate 12a (edge substantially perpendicular to surface face 16). Edges 17 of first plate 12a each comprise at least one protrusion 18 substantially perpendicular to said edge 17. Each protrusion 18 collaborates with an aperture 19 made in corresponding side wall 14b, 14c of mounting plate 14. According to the particular embodiment, each edge 17 comprises two protrusions and each side wall comprises two corresponding apertures. The apertures and protrusions on the one hand enable the mounting plate to be kept mounted on first plate 12a, and on the other hand enable the travel of mounting plate 14 to be limited with respect to first plate 12a. In other words, a protrusion passes at least partially through the associated aperture to form a stop for movement of mounting plate 14 with respect to the first plate. The transverse dimensions of the protrusion are substantially equal to the transverse dimensions of the aperture perpendicularly to the longitudinal axis of the side walls.

In order to block first plate 12a with second plate 12b, mounting plate 14 can comprise two recesses 20a, 20b forming the first engagement means, at an end directed towards second plate 12b (FIG. 8), each recess being made at the level of a side wall of mounting plate 14 and running along the longitudinal axis of mounting plate 14. In the first position, each recess 20a, 20b collaborates with a corresponding lug 21 of second plate 12b which is then housed in the associated recess. Lug 21, forming the second engagement means, is formed salient from an edge of second plate 12b.

Mounting plate 14 is preferably constantly biased in the direction of the plate on which it is not fitted, for example by biasing element such as a spring.

This embodiment can be implemented as for example in FIG. 9 in which first plate 12a comprises a through opening 22 made at the level of one of its surfaces perpendicularly to the plane of said first plate 12a. The base of the mounting plate then comprises a protuberance 23 able to move in opening 22, between the two sides walls 14b, 14c, said protuberance 23 then being connected to an inner surface of the opening by a spring 24 so as to stress movement of mounting plate 14 in an opposite direction to the first element (in the direction of arrow F1 in FIG. 8). In FIG. 8, spring 24 is a compression spring and the latter connects protuberance 23 to a distal inner surface of the opening of hinge 13. The person skilled in the art can naturally also use a tension spring secured to the protuberance and to an inner face of the proximal opening of hinge 13.

The user of the prosthesis can thus pull on the mounting plate in an opposite direction to arrow F1 to disengage the recesses from their respective lugs and to move the prosthesis to the second position of rod 8. To be able to return to the first position, the user can perform the reverse action. In preferential manner, the ends of side walls 14b, 14c of mounting plate 14 at the level of the recesses and facing the associated lugs each comprise a bevel enabling automatic latching of the recesses with the lugs when the user resumes a standing position. Rod 8 tends to return to the first position, when returning on the feet up position, and the bevel then comes into contact with an associated lug, naturally pushing mounting plate 14 in an opposite direction to arrow F1 until engagement is achieved. In other words, in general manner, the first and second engagement means can be formed in such a way as to engage automatically when extension of the prosthesis takes place when the latter is in the second position.

This involves an example embodiment, the person skilled in the art naturally being able to modify the assembly, for example by reversing assembly of the first plate and of the second plate respectively on the rocker and on the support part.

According to a development, the absorbing system comprises a jack. The jack is preferably of oleo-pneumatic type. It preferably enables distinct adjustment of its compression force and of its speed of expansion. In other words, the jack can comprise distinct means for adjusting its compression force and its speed of expansion. For example, the speed of expansion can be adjusted to provide a softer return from the flexion position to the extension position. This enables, in particular, the lower limb to be adjusted according to the level and the desire of the user.

By extension, when referring to a lower limb prosthesis, the element for receiving a thigh stump, the support part and the leg are mechanical elements enabling an amputated person, for example a skier, to find his bearings on both of his lower limbs, and to perform functions close to that of a real lower limb under particular conditions such as the triple flexion position (hip, knee, ankle). For this, the pins referred to above (pivot link pin, assembly pins of the rod on the support part and on the rocker, assembly pin of the absorbing system on the rocker and swivel pin of the rocker), are all preferably substantially parallel to one another.

Figure 10:
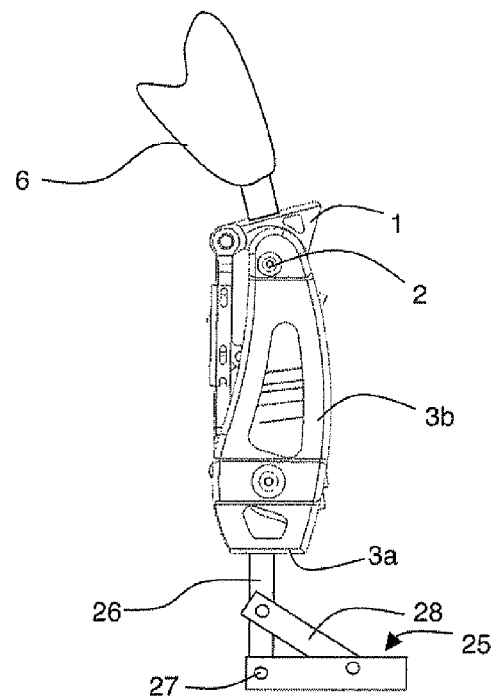
FIG. 10 illustrates a particular embodiment of a lower limb.

As illustrated in FIG. 10, the prosthesis can further comprise a foot 25 fitted on one end of leg 3 opposite support part 1, for example on a rod 26 of the leg fixed to the main body 3a, 3b, 3c opposite the support part. Foot 25 is pivotally mounted on said leg 3, the axis of pivoting then being substantially parallel to the pin of pivot link 2 forming the joint. Rod 26 can be assembled on foot 25 by a pin 27 at the level of the area called the instep. Rod 26 can be connected by means of a jack 28 with one end of foot 25 opposite rod 26.

The use of jack 28 at the level of the foot enables a compensation of the flexion of the prosthesis to be obtained at the level of the joint by a dorsal flexion of the foot.

According to an alternative embodiment (not shown), a sole is fitted on a bottom surface of the foot, said sole taking a shape designed to collaborate with a binding for a ski boot.

In the particular case of snow sports, the amplitude of movement provided by such a prosthesis enables the user to adapt to any type of skiing or snow surfing.

Support part 1 can comprise a preferably flat surface opposite the joint (pivot link 2) designed for fixing element for receiving 6 to a thigh stump. The element for receiving 6 can comprise a plate, for example fixed to said surface by screws. The plate of the element for receiving is itself fixed to a receptacle, for example made from carbon fiber, shaped in the same way as the stump of the user's lower limb.

Tests carried out on this prosthesis using a jack as absorbing system have enabled it to be shown that, with an angle of flexion a of 155 degrees, the force exerted by the jack is about 2200 N Newton, whereas with an angle of flexion a of 110 degrees, the force $F_{jack}$ exerted by the jack of the absorbing system is about 3340 N. In other words, compared with the prior art, the prosthesis described above enables a substantially constant absorbing force to be kept on the jack whatever the angle of flexion at the knee, in particular due to the use of a restoring force. Thus, unlike the prior art, this prevents absorbing from being lost and procures an improved user comfort approaching that of a valid lower limb.

Apart from the fact that the prosthesis is more robust, keeping a substantially constant force at the level of the absorbing system whatever the angle of flexion a of the prosthesis enables enhanced performances to be achieved throughout a ski run. This in particular makes it possible to press on the prosthesis while at the same time keeping a high level of control of the ski even when pressing is unilateral.

Figure 11:
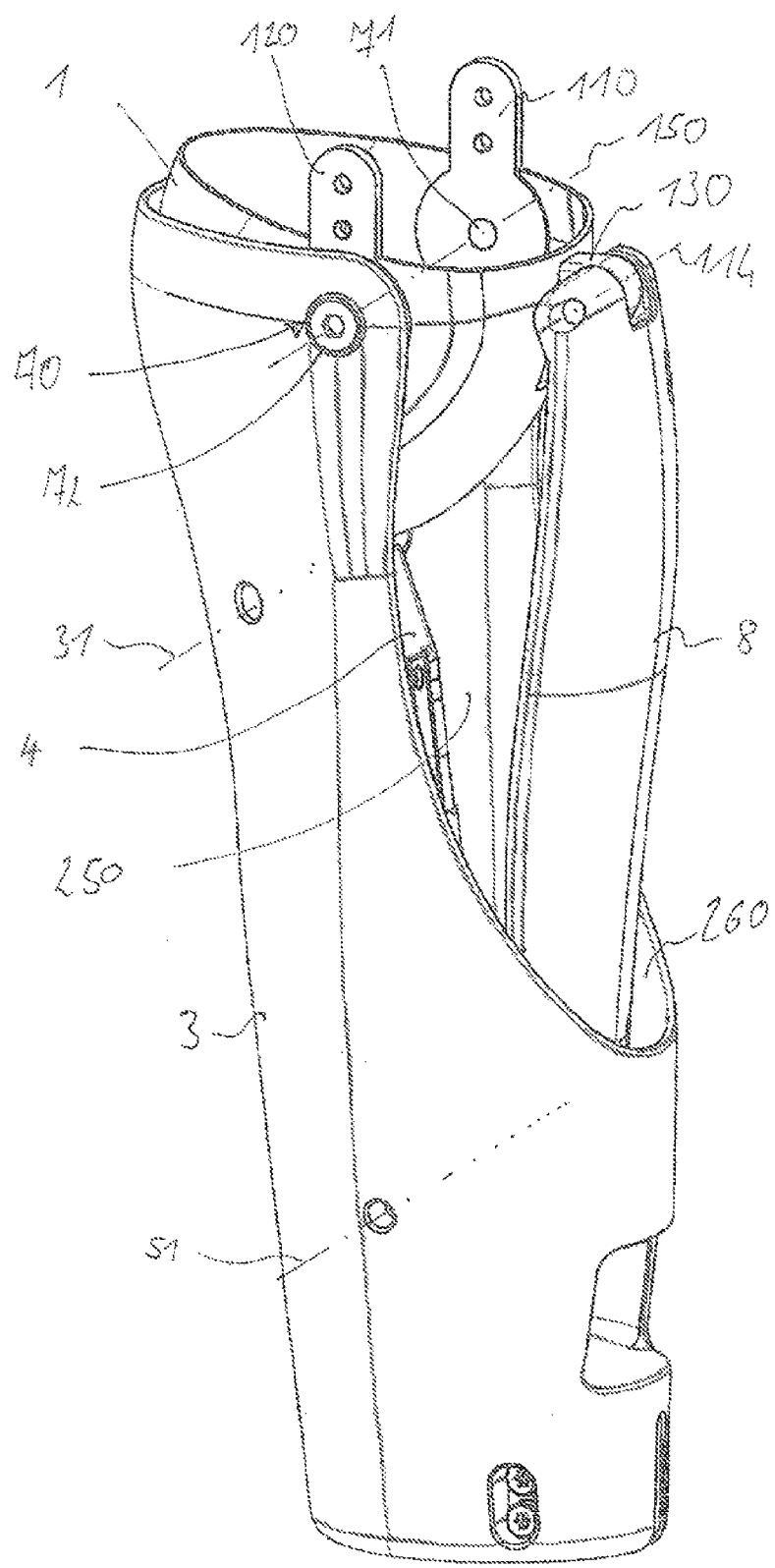
FIG. 11 illustrates a scenographic view of a particular embodiment of the prosthesis.

FIG. 11 illustrates an alternative embodiment of an above knee prosthesis comprising a support part 1, fitted to receive a stump or for mounting a receiving element, which is designed to receive a thigh stump, especially a stump with a disarticulated shank. The receiving element or the support part can be a prosthetic shaft for encircling the stump, lateral rails or splint with belts and hook and loop fasteners for fitting the receiving element to the stump, or as a support part for an osseointegratable implant device. The osseointegratable implant device can be established by or fixed at the support part. The support part 1 can receive the stump directly or with a liner, fixed to the support part by a pin or low pressure. If the receiving element is different to the support part, it can be fitted onto the support part by lateral lugs or brackets 110, 120. The lugs or brackets 110, 120 are fixed at the support part 1, the receiving element can be fixed to the lugs or brackets 110, 120 by screws, bolts or other positive locking means. The receiving element can also be fixed on the cup shaped support part 1 by gluing, welding or form fitting elements like a shuttle lock or a pin or by magnetic holders.

A distal prosthetic part 3 in form of a prosthetic shank is assembled on the support part 1 by a pivot link, forming a pivot joint 2 so that the distal prosthetic part 3 can be pivoted around a joint axis 150 for flexion or extension of the distal prosthetic part. The joint axis 150 is orientated in medial-lateral direction, preferably through the lugs or brackets 110, 120. Bearing points 71, 72 are provided on medial and lateral parts of the support part 1 and distal prosthetic part 3, so that a pivot link 2 or a pivot joint 2 is established. The distal prosthetic part 3 is hollow and comprises an inner space 250.

An absorbing system 4 is arranged inside the inner space 250. The absorbing system can comprise at least a dampening device, a spring arrangement and/or an actuator device. In the shown embodiment, the absorbing system 4 is a hydraulic dampening device with a proximal fixing or bearing point that is positioned distal to the support part 1. The proximal bearing point enables a swiveling movement of the dampening device 30 around an axis 31 that is orientated parallel to the joint axis 150.

On a rear, posterior part of the support part 1, a protrusion 130 is positioned for receiving and supporting a rod 8. The rod 8 is positioned posterior to the joint axis 150 and can swivel around an axis 114. Axis 114 is spaced apart from the joint axis 150 so that upon rotation of the support part 1 around the joint axis 150 the upper part of the rod 8 performs an orbital movement. Therefore, the rod 8 performs a movement in a vertical and a horizontal direction.

Figure 12:
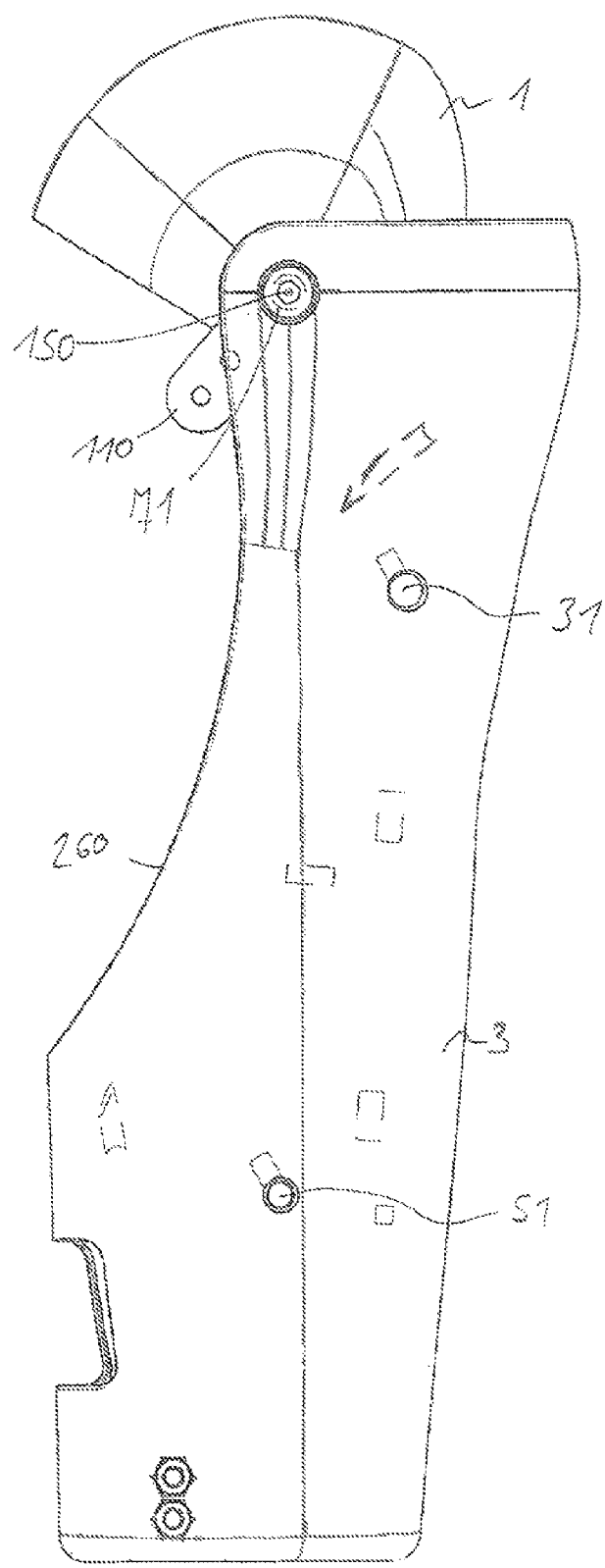
FIG. 12 illustrates a lateral view of a prosthesis without absorbing system.

FIG. 12 illustrates a lateral view of a prosthesis without the posterior rod 40. The proximal axis 31 of the absorbing system 4 as well as a distal rotation axis 51 of a lever (not shown in FIG. 12) can be seen. The position of both axes 31, 51 can be altered in or on the distal prosthetic device 3, so that the distance and orientation of the axes 31, 51 can be adjusted and fixed in the adjusted position.

Figure 13:
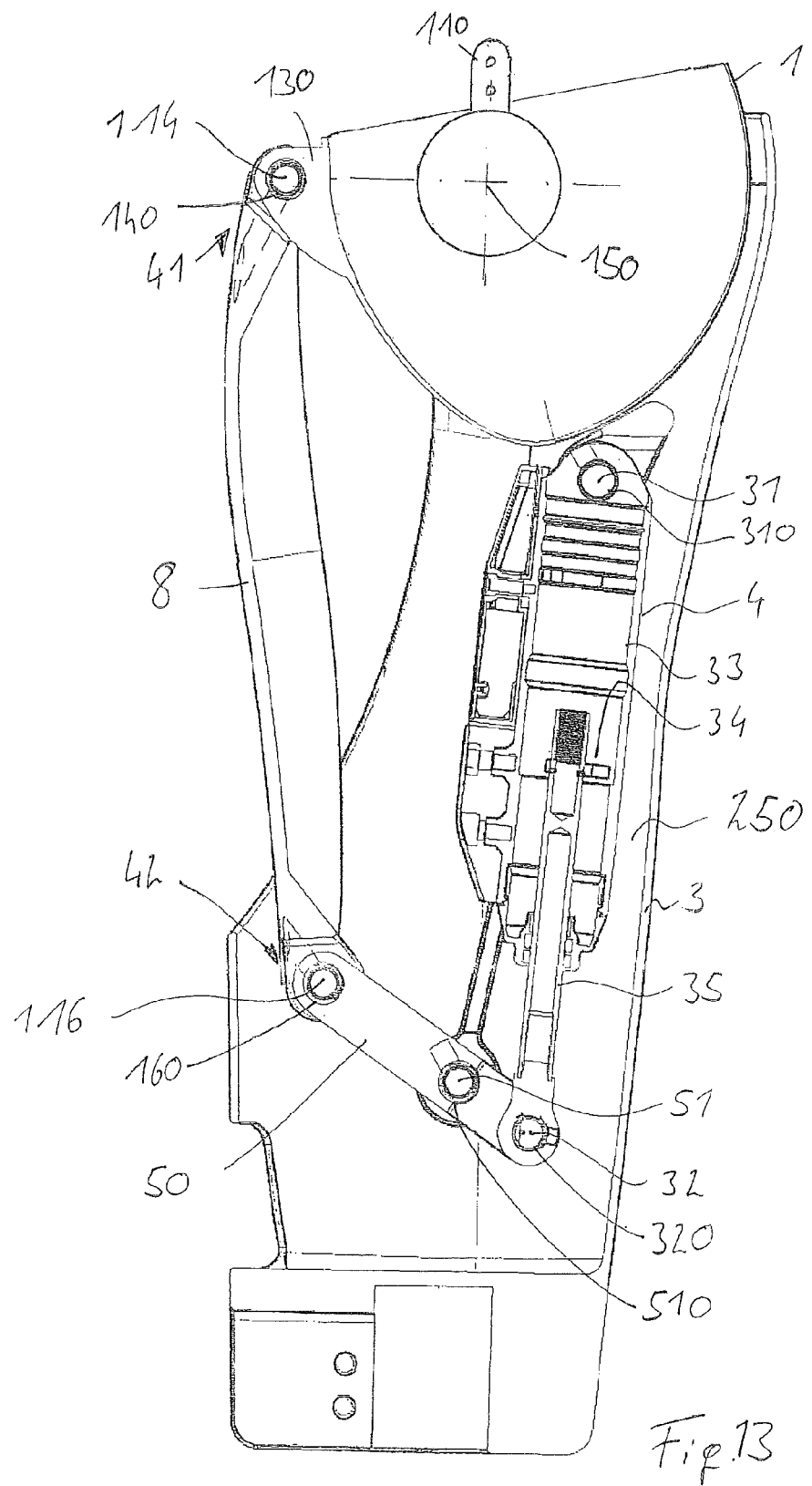
FIG. 13 illustrates a sectional view of a prosthesis in extended position.

In FIG. 13 a sectional view of the prosthesis is shown. The cup shaped support part 1 can receive a thigh stump, a shank stump or an upper arm. The protrusion 130 is positioned at the posterior part of the support part and fitted to receive a pin or stud to form a bearing point 140 for a pivotal support of the rod 8. Rod 8 is connected with its proximal area, more precisely with the proximal end 41 at the bearing point 140 with the support part. The opposing, distal end of the rod 8 is supported on a lever 50. Lever 50 is pivotally supported at the distal prosthetic part 3. Lever 50 has two arms, one on each side of a pivot axis 51 and establishes a rocker. Rod 8 forms with lever 50 a bearing point 160, so that the lever 50 will be pivoted when the rod 8 is actuated by flexion or extension of the support part 1 around the joint axis 150.

On the opposing lever arm, i.e. the lever arm on the other side of the pivot axis 51, the distal or lower end of the absorbing system 30 is mounted in a lower bearing point 320. The lever 50 itself is mounted pivotally inside the hollow inner space 250 of the distal prosthetic part 250 at the bearing point 510. Bearing point 320 enables a swiveling movement between the piston rod 35 and the lever 50 so that the piston rod 35 can perform a linear movement if the lever 50 swivels around the pivot axis 51. This leads to a linear movement of the piston 34, which is coupled with the piston rod 35 inside the hydraulic cylinder 33. The upper end of the absorbing system 4 is pivotally mounted at the upper bearing point 30 thereby forming an axis 31 of rotation.

In the shown embodiment of FIG. 13, the bearing points 140, 160, 310, 320, 510 of the components are set. In an alternative embodiment the bearing points 140, 160, 310, 320, 510 are adjustable, either steplessly or stepwise adjustable, so that the respective components can be arranged in different orientations, locations and distances to each other to adapt the arrangement to requested requirements. By changing the distances between the bearing point 160, 320 of the rod 8 and the absorbing system 4 on the lever 50, the leverage ratio of the rocker can be altered so that the travel of the piston 34 and the piston dead center is adjustable. Furthermore, rods 40 of different lengths or length adjustable rods can be used, such as, for example, telescopic rods, rods with threaded sleeves, or rods with adapters. By this it is possible to change the characteristics of the adsorbing system, the piston dead center of a hydraulic damper, and the force ratios.

Figure 14:
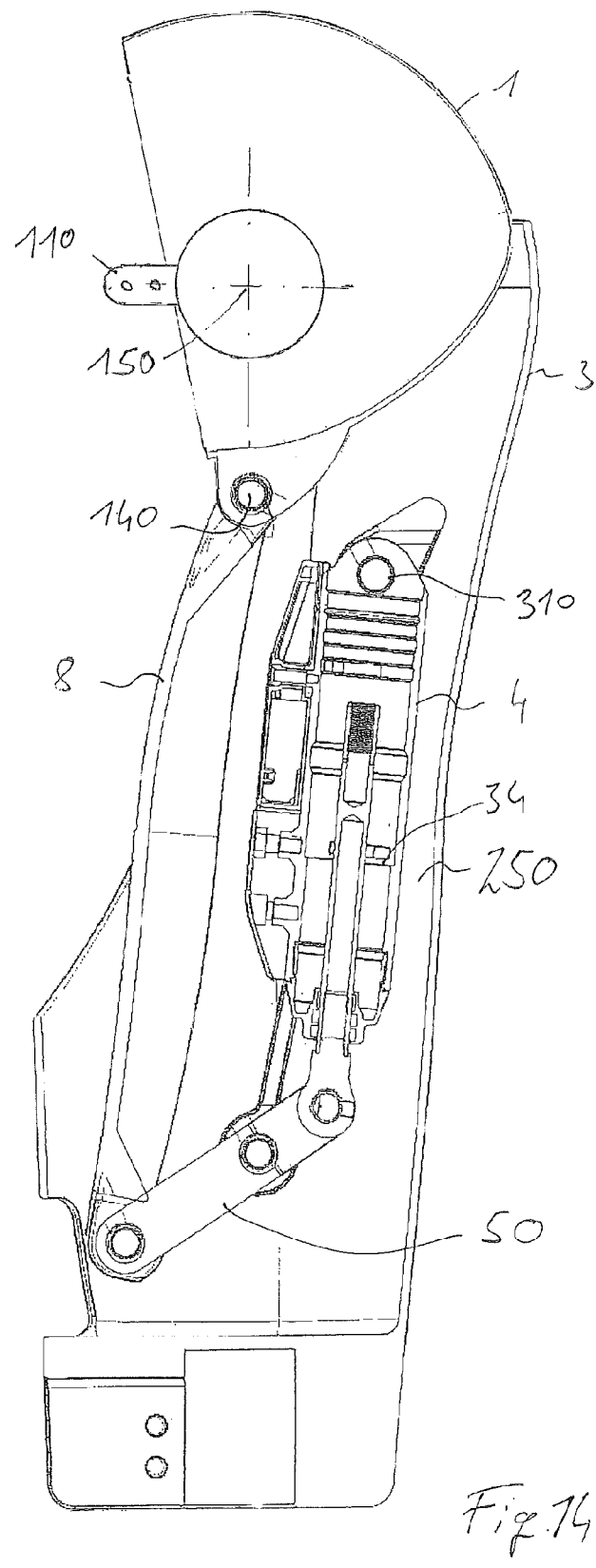
FIG. 14 illustrates a prosthesis according FIG. 13 in 90° flexed position.

FIG. 14 shows the prosthesis in a flexed position in which the support part 1 is flexed about 90° relative to the distal prosthetic part 3 compared with the maximum extended position shown in FIG. 11. Because of the orbital path of the upper bearing point 140 of the rod 8, the rod 8 is swiveled relatively to the support part 1 and is moved in an anterior direction as well as in a distal direction, causing a counterclockwise swiveling movement of the lever 50 around pivot axis 51. This causes an upwardly directed movement of the other lever arm and the bearing point 320 of the piston rod 35 in the direction of the upper bearing point 310. By this, the piston 34 is moved inside the cylinder 33.

Figure 15:
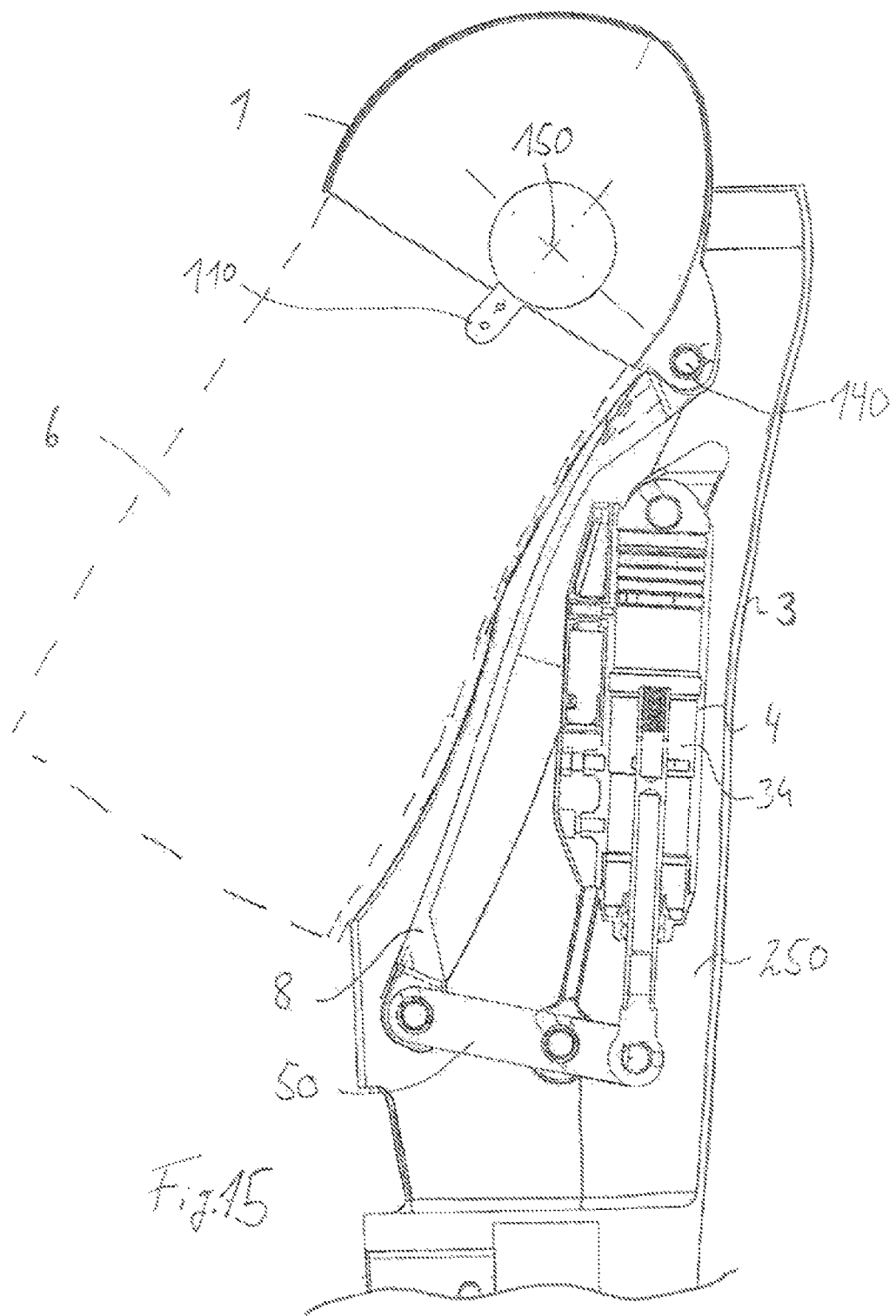
FIG. 15 illustrates a prosthesis according FIG. 13 in maximal flexed position.

FIG. 15 shows the prosthesis in its maximal flexed position. Support part 1 is swiveled around the joint axis 150 so that a receiving element 6 (shown in dotted lines) contacts the rear or posterior part of the distal prosthesis part 3. Rod 8 is moved back into a distal direction because the upper bearing point 140 is moved after reaching its most distal point of motion in an upward direction so that the lever is rotated in a clockwise direction coming from the position shown in FIG. 14. This leads to a reversal of movement of the piston 34 in the cylinder 33. With different resistances in the damper for upward and downward movement by choosing different valves or throttles it is possible to provide the damper with different resistances according to the direction of movement. From a maximal extended position as shown in FIG. 13 to the 90° flexed position according to FIG. 14, the piston moves upwardly up to its uppermost position. When flexing the support part further into the position of FIG. 15 or if the support part is moved back in an extension direction, the piston 34 reverses its movement and can provide a lesser resistance than in the other direction.

As already mentioned the absorbing system 4 can be equipped with at least one of the group consisting of a damper, a spring or an actuator (e.g., a motor, electro magnet or the like). Such absorbing system is arranged at least partially inside the hollow inner space 250 of the distal prosthetic device, which is formed like a tube with an outer appearance of the limb to be replaced. The lever 50, as well as the piston rod 35 and the rod 8, can be variable in their length, for example by threaded sleeves. A variation of the length can be provided by a number of mounting points on the lever 50 or rod 8.

Besides an adjustment of the bearing points 140, 160, 320, it is possible to adjust the bearing points of the lever 50 and the absorbing system 4 in or on the distal prosthetic device 3. In other words, it is possible to position the bearing points 140, 160, 320 at different spots or places on the prosthetic device 3 and to fix them at the respective spots. The static and dynamic set up of the prosthesis is changed by the arrangement of the bearing points 310, 520.

The AKP (above knee prosthesis) according to the embodiments of FIG. 11 to FIG. 15 is especially suited for patients with a knee disarticulation, since the stump can protrude in the clear space of the cup shaped support part 1 so that the joint axis 150 of the pivot link 2 can be located in the position of the natural joint of the sound leg. The position of the joint axis 150 can be individually chosen by placing the bearing points 71, 72 at the support part 1 or at the receiving device 6. The distal prosthetic device 3 has at its upper ends medial and lateral flanges which are arranged left and right to the support part 1 and establish corresponding bearing points. Since AKP for knee disarticulated patients cannot be adjusted in their proximal set up by pyramidal adapter, the bearing points may be adjustable. Furthermore, the lever 50 can be designed as a multipart lever with at least two lever parts or lever branches, which can be rotated relative to each other about an axis to change the angle between the lever parts. By changing the angle, the distance between the bearing points 160, 320 can be altered as well as the distance between the lever parts and the bearing points 140, 310 of the rod 8 and the absorbing system on the leg 3. The axis of the multipart lever is preferably parallel or identical with the swivel axis 51 of the lever 50. By alternation of the angle between the lever parts it is possible to change the position of the reversal point or piston dead center point and to alter the damper characteristics or actuation characteristics of the absorbing system 4.

FIG. 16 shows some diagrams of a damping force over the knee angle depending on different length of the hydraulic damper 4 and the rod 8. The uppermost graph in the upper diagram depicts the dampening force with a long rod 8, the middle graph is for a little shorter rod, and the third graph shows the dampening force with a shortest rod. Depending on the length of the rod and the dampening device the piston dead center is reached at different knee angles. As the rod is lengthened, the piston reaches dead center sooner, which means that the lowest dampening is reached earlier compared with shorter rods. This is because the dampening force decreases in the area of the piston dead center. It is advantageous that the dead center point is located in the area of about 90° flexion, which is an angle normally present when sitting.

The lower diagram shows the dampening characteristics for different positions of the bearing points and length of the rod and the absorbing system. This diagram illustrates that it is possible to adjust the dampening characteristics by amending the geometric positions and orientations of the components of the prosthesis.

By amending the length of the lever or lever branches and the position of the piston rod or the absorbing system it is possible to adjust an extension stop of the prosthesis. This can be reached by adjusting the absorbing system, e.g. by adjusting the length of the piston rod or by adjusting the length of the rod 8. Furthermore, it is possible to design the lever or rocker 50 as a two-part lever with two branches which can be pivoted or rotated relative to each other so that by amending the orientation of the lever arms or branches it is possible to adjust the position and the relative length of the rod and the absorbing system.

The dampening characteristics of the absorbing system 30 are previously adjusted in accordance to the joint angle (e.g., especially a knee angle) so that the dampening characteristics are optimized for the intended purpose of the prosthesis.

FIG. 17 schematically illustrates the arrangement of the components according to FIGS. 13 to 15. The pivot joint axis 150 is positioned proximally to the distal end of the support part 1 so that an adjustment or correction of the length of a prosthetic shaft can be carried out easily since the bearing points 71, 72 of the pivot link 70 can be located almost freely along the longitudinal direction of the support part 1. It is possible to arrange the pivot axis 150 in an area of a natural joint axis so that it is possible to provide a patient with almost equal limb parts so that a more natural movement can be carried out with a prosthesis according to the claimed invention. Besides an embodiment as shown for patients with a knee disarticulation it is possible to fit such prosthesis on a shank stump or an upper arm stump. The lever 15 according to this embodiment is designed as a rocker with two lever branches 52, 53, the rod 8 is arranged at the rear lever branch 53, and the absorbing system 3 is arranged on the opposite lever branch 52. The lever 15 or rocker is pivotally supported and can be pivoted around the swivel axis 51. The bearing points 160, 320 of the absorbing system 3 and the rod 8 can be adjusted as well as the bearing point of the rocker 50.

FIG. 18 schematically illustrated an alternative embodiment comprising a single arm lever 50 on which the bearing points 320, 160 of the absorbing system 4 and the rod 8 are located on the same side of the swivel axis 51. The bearing points 160, 320 are spaced apart from each other and can be located at different positions on the lever 50. By adjusting the distance between the bearing points 160, 320 and the position of the bearing parts 160, 320 is it possible to change the force ratio as well as the path ratio. The upper bearing point 310 of the absorbing system 4 is arranged above at a proximal point compared to the swivel axis 51.

A further alternative embodiment is shown in FIG. 19. The difference between FIG. 18 and FIG. 19 is that in FIG. 19 the bearing point 310 of the absorbing system 4 on the leg 3 or distal prosthetic part 3 is distal to the bearing point 510 of the lever 50. Such an arrangement is advantageous if the swivel axis 51 has to be positioned very near to the support part 1 so that no room is left for positioning the absorbing system 4. As in the previous embodiments, the bearing points 510, 320, 310 and 160 can be relocatable on the lever 50 or at the distal prosthetic part 3.

A further embodiment is shown in FIG. 20 with a bearing point 510 of the lever 50 in the middle or posterior part of the distal prosthetic part 3. The bearing point 310 of the absorbing system 4 is arranged distally to the bearing point 510 and in the posterior part of the leg 3. Rod 8 when in an extended position is positioned outside of the inner space 25 of the low leg 3.

FIG. 21 illustrates a further embodiment with a rod 8 crossing absorbing system 4. With such an arrangement having a single arm lever 50 with its bearing point 510 at the distal prosthetic part 3 it is possible to introduce a rod 8 in the inner space 25 near the upper end so that it is protected by the prosthetic part 3. By rotating the support part 1 around the pivot axis 150, lever 50 turns counterclockwise so that the absorbing system is under tensile load. By reversing the movement of the rod 8, the absorbing system 4 is under compressive load.

FIG. 22 illustrates a further embodiment of the claimed invention in which bearing point 510 of single arm lever 50 is located posterior to the joint axis 150, lever arm protrudes in an anterior direction and rotates counterclockwise when support part 1 is rotated clockwise for flexion. This embodiment enables a positive path ratio for the absorbing system 4 which means that the distance between the upper bearing point of the rod 8 and the joint axis 51 can be comparatively small. The double arrows indicate the possible adjustment path along the longitudinal direction of lever 50.

A further embodiment is shown in FIG. 23, in which the absorbing system is not fixed to the lever 50 but to the rod 8 in its distal part 42. Lever 50, with its bearing point 510 proximal to the bearing point 310 of the absorbing system 4 on the leg 3, provides guidance of the rod 8 and absorbing system 4. The bearing point 320 can be moved along the rod 8. A gear ratio regarding force and path is established because of the specific orientation of the angles of the rod 8 and the longitudinal direction of the absorbing system 4.

FIG. 24 illustrates a variation of FIG. 23 with the absorbing system 4 providing recourse to dampening devices like hydraulic or pneumatic dampers. It is understood that the absorbing system can compare or be established by spring devices and/or actuators as well.

Especially FIGS. 11 to 15 show that rod 8 is guided into the inner space 250 of the distal prosthetic part 20. A distal prosthetic part 20 has a tube-like form with an outer appearance similar to a natural limb (e.g., the embodiment of FIGS. 11 to 15 in the form of a shank). A distal prosthetic part 3 is provided with a cutout 260 which is at least partly covered by a rod 8. Rod 8 completes the outer contour of the distal prosthetic part 3. Furthermore, the cutout 260 enables the support part 1 and the receiving element 6 to conduct a flexion movement greater than 90°. Such a position is shown in FIG. 15. Rod 8 is located posterior to the pivot axis 150 and in front of the cutout 260 and acts like a cover for the absorbing system 4 and the lever mechanics. Furthermore, it is a contour completing part of the prosthesis.

Absorbing system 4 can be a damper alone or a combination of a damper with a spring unit and/or an actuator unit which can be established as a motor and can provide a driving or decelerating effect of the prosthetic joint. The absorbing system can be controlled mechanically without electronic devices. In the alternative, it is possible to provide a control with an angle sensor and a torque sensor more precisely with a knee angle sensor and torque sensor for determining the torque had an ankle joint. Furthermore it is possible to provide a control by an inertial sensor arranged in the distal prosthetic part 3 in combination with a hydraulic dampening system which locks the joint if a load is exerted. Furthermore, a combination with an inertial sensor in the distal prosthetic part 3 in combination with a torque sensor in the pivot joint 2 can be used together with a force sensor for determining a force acting along the piston rod or on the bearing points 310, 320 of the absorbing system. Furthermore, such a force can be determined by measuring the pressure in the hydraulic circuit of a dampening system.

Inertial sensors can be provided in the support part 1, in the receiving element 6, as well as in the distal prosthetic part 3. Inertial sensors can be established by a gyroscope as well as acceleration sensors and combinations of both sensor types. Force sensors can be established by strain gauges, pressure sensors can be established by piezo elements, and angle sensors can be established by Hall-effect sensors.

By providing the prosthesis with a rod in combination with a lever it is possible to significantly reduce the stroke of travel of piston in the damper or the actuator. A reduction of the stroke or travel of a piston leads to a reduction of the length of the cylinder or housing so that the absorbing system 3 can be shortened by the double of the reduction of the stroke or travel. This is of great importance in prosthetic devices with restricted installation space.

By amending the length of the rod 8 as well as by extending or shortening the absorbing system or adjusting the angular position of the lever branches it is possible to amend and adjust the position and orientation of the support part 1 and by this of the receiving element 60 and the set-up of the complete prosthesis. The support part 1 can be cup-shaped so that it is possible to support a stump directly, if necessary with advanced prosthetic shaft concepts. Since the pivot axis 150 is located on the support part 1 proximal to the distal end of the support part 1 it is possible to locate the joint axis 150 along the longitudinal direction of the stump, receiving element 6, or support part 1. By this it is possible to locate the pivot axis in the area of a natural joint as well as proximal on the support part 1 or receiving element 6. By locating the pivot axis 150 proximal as much as possible, the moment of inertia of the distal prosthetic part 3 is reduced so that the patient is provided with a subjective lighter prosthesis.

FIG. 25 illustrates an embodiment of a two-part-lever 50 comprising a first lever branch 52 and a second lever branch 53 which are pivotally connected and can rotate around a common swivel axis 51. Each of the lever branches 52, 53 is provided with a side arm 56, 57. Threads are provided in the side arms 56, 57 in which screws 54, 55 are arranged. Screws 54, 55 are adjustment screws, wherein one of the screws acts to a tensioning element to pull the side arms 56, 57 to each other whereas the other screw acts as a fixing device and acts against the first screw so that the side arms 56, 57 are braced against each other. In the position according FIG. 25, the respective bearing points 160, 320 are in their maximal distance and the lever branches 52, 53 form a straight rocker.

FIG. 26 illustrates the lever 50 of rocker 50 in a pivoted position, and the tension screw 54 is driven in the side arms 56, 57 so that the side arm 56, 57 are moved towards each other which leads to a rotation of the lever branches 52, 53. This in turn leads to an adjustment of the position of the bearing points 160, 320. The distance between the bearing points 160, 320 is reduced, the position of the rod (not shown) relative to the absorbing system (not shown) is adjusted correspondingly.

FIG. 27 illustrates a further embodiment of the lever 50, wherein instead of screws 54, 55 several bores or drilled holes 58 are arranged circularly around the swivel axis 51. The bores or drilled holes 58 are provided in both lever branches 52, 53. With a formfitting element, for example a bolt or a pin, the orientation of the respective bores or drilled holes can be fixed after alternation and the position of the bearing points 160, 320 can be adjusted in the required position by amending the angular position of the lever branches 52, 53.

What is claimed is:

1. A prosthesis for a residual limb, comprising:
    an element for receiving a stump;
    a support part connected to the element for receiving a stump and configured to transfer forces in compression and tension;
    a distal prosthetic part connected to the support part with a pivot connection to form a joint to enable flexion or extension of the distal prosthetic part with respect to the element for receiving a stump;
    a lever pivotally connected to the distal prosthetic part;
    a rod directly connected to the lever and to the support part;
    an absorbing system to absorb flexion or extension forces, the absorbing system being connected at a proximal end to the distal prosthetic part and at a distal end to the lever.

2. The prosthesis according to claim 1, wherein the absorbing system comprises at least one of a dampening device, a spring device and an actuator device.

3. The prosthesis according to claim 1, wherein the support part comprises one of a prosthetic shaft, a cup shaped receiving element configured to be connected with a prosthetic shaft or a liner, or an osseointegratable device.

4. The prosthesis according to claim 1, wherein the lever comprises two lever arms on opposing sides of a pivot axis to establish a rocker, the absorbing system being fitted on a first lever arm, and the rod being fitted on a second lever arm.

5. The prosthesis according to claim 1, wherein the lever comprises a single lever arm, the absorbing system being fitted on the lever arm spaced apart from a fitting point of the rod on the lever arm.

6. The prosthesis according to claim 1, wherein the absorbing system or the rod are displaceably fitted on the lever.

7. The prosthesis according to claim 1, wherein at least one of the rod, the lever, and the absorbing system has a variable length.

8. The prosthesis according to claim 1, wherein the distal prosthetic device is hollow with an inner space in which the lever and the absorbing system are at least partially arranged.

9. The prosthesis according to claim 1, wherein the rod at least partially covers an opening in the distal prosthetic device.

10. The prosthesis according to claim 9, wherein the rod is formed to have an appearance of a natural limb.

11. The prosthesis according to claim 1, wherein the joint comprises a joint axis, and the joint axis runs through the support part.

12. The prosthesis according to claim 1, wherein the joint comprises a joint axis, and the joint axis is arranged in an area of a joint axis of a natural limb.

13. The prosthesis according to claim 1, wherein the joint comprises a joint axis, and the joint axis is arranged proximal to a distal end of the support part.

14. The prosthesis according to claim 1, wherein the distal prosthetic part is directly mounted on the support part at at least one bearing point, and the at least one bearing point is medially or laterally positioned on the support part.

15. Prosthesis according to claim 14, wherein the at least one bearing point is displaceably mounted on the support part.

16. The prosthesis according to claim 1, wherein the rod is displaceably mounted on the support part.

17. The prosthesis according to claim 1, further comprising a locking device configured to lock the flexion or extension of the distal prosthetic part with respect to the element for receiving.

18. The prosthesis according to claim 1, wherein the lever comprises two lever parts, the lever parts being displaceably fitted to each other.

19. The prosthesis according to claim 18, wherein the lever parts are pivotally fitted to each other, and a pivot axis of the lever parts align with a pivot axis of the lever.

20. The prosthesis according to claim 1, wherein the prosthesis is a prosthesis for a lower limb, the support part is for receiving a thigh stump or a thigh shaft, the joint forms a knee joint, and the distal prosthesis device is a shank part.

21. A prosthesis for a residual limb, comprising:
an element for receiving a stump;
a support part connected to the element for receiving a stump and configured to transfer forces in compression and tension;
a distal prosthetic part connected to the support part with a pivot connection to form a joint to enable flexion or extension of the distal prosthetic part with respect to the element for receiving a stump;
a lever pivotally connected to the distal prosthetic part;
a rod connected to the lever and extending to a connection point with the support part;
an absorbing system to absorb flexion or extension forces, the absorbing system being connected at a proximal end to the distal prosthetic part and at a distal end to the lever.

22. The prosthesis according to claim 21, wherein the rod is configured to transfer forces in compression and tension between the lever and the support part.

23. The prosthesis according to claim 1, wherein the rod is configured to transfer forces in compression and tension between the lever and the support part.

* * * * *